US011268105B2

(12) United States Patent
Perkins et al.

(10) Patent No.: US 11,268,105 B2
(45) Date of Patent: Mar. 8, 2022

(54) METHODS OF CELL RENEWAL

(71) Applicant: SynPloid Biotek, LLC, Savannah, GA (US)

(72) Inventors: Edward Perkins, Savannah, GA (US); Amy Greene, Savannah, GA (US); Dominique Broccoli, Savannah, GA (US)

(73) Assignee: CarryGenes Bioengineering, Savannah, GA (US)

( * ) Notice: Subject to any disclaimer, the term of this patent is extended or adjusted under 35 U.S.C. 154(b) by 88 days.

(21) Appl. No.: 15/844,014

(22) Filed: Dec. 15, 2017

(65) Prior Publication Data

US 2018/0171355 A1    Jun. 21, 2018

Related U.S. Application Data

(60) Provisional application No. 62/434,934, filed on Dec. 15, 2016.

(51) Int. Cl.
| | |
|---|---|
| *C12N 15/85* | (2006.01) |
| *C12N 9/80* | (2006.01) |
| *C12N 15/90* | (2006.01) |
| *C07K 14/47* | (2006.01) |
| *C12N 9/12* | (2006.01) |

(52) U.S. Cl.
CPC .......... *C12N 15/85* (2013.01); *C07K 14/4702* (2013.01); *C12N 9/1276* (2013.01); *C12N 9/80* (2013.01); *C12N 15/907* (2013.01); *C12Y 207/07049* (2013.01); *C12Y 305/01* (2013.01); *C12N 2800/30* (2013.01); *C12N 2830/003* (2013.01)

(58) Field of Classification Search
None
See application file for complete search history.

(56) References Cited

U.S. PATENT DOCUMENTS

| | | | |
|---|---|---|---|
| 8,865,124 B2 * | 10/2014 | Miyawaki ............... | C07K 14/00 424/1.11 |
| 2002/0160410 A1 | 10/2002 | Hadlaczky | |
| 2004/0096891 A1 | 5/2004 | Bennett | |
| 2005/0164969 A1 * | 7/2005 | Blander ............. | C07K 14/4746 514/44 R |
| 2005/0181506 A1 | 8/2005 | Perkins et al. | |
| 2007/0004002 A1 | 1/2007 | Okazaki | |
| 2011/0318832 A1 * | 12/2011 | Cech .................... | C12N 9/1241 435/366 |
| 2012/0064578 A1 | 3/2012 | Perkins et al. | |
| 2012/0093785 A1 | 4/2012 | Oshimura et al. | |
| 2014/0079836 A1 | 3/2014 | Mcdaniel | |
| 2014/0295501 A1 | 10/2014 | Katona et al. | |
| 2016/0115455 A1 | 4/2016 | Mikkelsen et al. | |
| 2018/0010150 A1 | 1/2018 | Perkins et al. | |

FOREIGN PATENT DOCUMENTS

| | | |
|---|---|---|
| EP | 1559782 A1 | 8/2005 |
| EP | 2218786 A4 | 6/2011 |
| EP | 2522725 B1 | 10/2016 |
| EP | 1559782 B1 | 12/2016 |
| WO | 9740183 A2 | 10/1997 |
| WO | 0018941 A1 | 4/2000 |
| WO | 2006066247 A2 | 8/2006 |

OTHER PUBLICATIONS

International Search Report and Written Opinion dated Apr. 24, 2018 in PCT/US17/66741.
Toutain et al., "Reduced Placental Telomere Length during Pregnancies Complicated by Intrauterine Growth Restriction", PLOS One, (Jan. 11, 2013), vol. 8, No. 1, pp. 1-8, XP055509501.
Basu, J., "Artificial and Engineered Chromosomes: Non-integrating Vectors for Gene Therapy." Trends in Molecular Medicine, Elsevier Current Trends, vol. 11 (5), pp. 251-258 (2005).
Ikeno, M et al., "Construction of YAC-based mammalian artificial chromosomes", Nature Biotechnology, (19980500), vol. 16, No. 5, pp. 431-439, XP009060040.
Katoh, et al., (2004) "Construction of a novel human artificial chromosome vector for gene delivery." Biochem. Biophys. Res. Comm. 321:280-290.
Kazuki, et al., "Refined human artificial chromosome vectors for gene therapy and animal transgenesis." Gene Therapy, vol. 18(4):384-393 (2010).
Kazuki, Y et al., "Human Artificial Chromosomes for Gene Delivery and the Development of Animal Models", Molecular Therapy, (2011) 19(9):1591-1601. doi:10.1038/mt.2011.136, XP055581607.
Kouprina et al., (2013) "A new generation of human artificial chromosomes for functional genomics and gene therapy", Cell Mol Life Sci., vol. 70, No. 7, pp. 1135-1148, XP055470579.
Kouprina, et al., (2014) "Human Artificial Chromosome-Based Gene Delivery Vectors for Biomedicine and Biotechnology." Expert Opinion on Drug Delivery. 11(4):517-535.
Kurosaki, et al., "Integration-free arid stable expression of FVIII using a human artificial chromosome." Journal of Human Genetics, vol. 56 (10), pp. 727-733 (2011).
Lindenbaum et al., "A mammalian artificial chromosome engineering system (ACE System) applicable to biopharmaceutical protein production, transgenesis and gene-based ceil therapy," Nucleic Acids REsearch, (2004), vol. 32, No. 21, pp. e172 1-15.
Martella, et al., "Mammalian Synthetic Biology Time for Big MACS," ACS Synthetic Biology, vol. 5, No. 10, pp. 1040-1049.
Ren, X et al., "A Novel Human Artificial Chromosome Vector Provides Effective Cell Lineage-Specific Transgene Expression in Human Mesenchymal Stem Cells", Stem Cells, (Nov. 1, 2005), vol. 23, No. 10, doi:10.1634/stemcells.2005-0021, pp. 1608-1616, XP055473399.

(Continued)

*Primary Examiner* — Channing S Mahatan

(74) *Attorney, Agent, or Firm* — Susan Myers Fitch

(57) ABSTRACT

The present invention encompasses compositions and methods to rejuvenate cells by, expanding the replicative life span of the cells for, e.g., use in regenerative therapies. Specifically, the methods and compositions of the present invention increase the proliferation capacity and differentiation capacity and plasticity of cells.

25 Claims, 5 Drawing Sheets

(56) References Cited

OTHER PUBLICATIONS

Rocchi, et al., (2010) "*Escherichia coli*-Cloned CTFR Loci Relevant for Human Artificial Chromosome Therapy." Human Gene Therapy, 21:1077-1092.
Takiguchi, et al., "A Novel and Stable Mouse Artificial Chromosome Vector." ACS Synthetic Biology, vol. 3 (12), pp. 903-914 (2014).
Teruhiko Suzuki et al., "A Novel System for Simultaneous or Sequential Integral of Multiple Gene-Loading Vectors into a Defined Site of a Human Artificial Chromosome," PLOS ONE, vol. 9, No. 10, pp. 1-9.
Toth, et al., "Novel Method to Load Multiple Genes onto a Mammalian Artificial Chromosome." Plos One, Public Library of Science, US, vol. 9 (1), pp. e85565-1 (2014).
Vanderbyl, S et al., "Transfer and Stable Transgene Expression of a Mammalian Artificial Chromosome into Bone Marrow-Derived Human Mesenchymal Stem Cells", Stem Cells, (20040500), vol. 22, No. 3, doi:doi:10.1634/stemcells.22-3-324, pp. 324-333, XP002506658.
Yamaguchi, et al., 2011 "A Method for Producing Transgenic Cells Using a Multi-Integrase System on a Human Artificial Chromosome Vector." PLoS ONE 6(2): e17267. https://doi.org/10.1371/journal.pone.0017267.
Brown and Glass, 2020, "Technology used to build and transfer mammalian chromosomes." *Experiments Cell Research* 388:111851.
European Search Report dated Jun. 10, 2020 in EP 17880348.2.
Gamble and Barton, 2012, "Baculoviral Expression of Telomerase in Primary Human Fibroblasts to Rejuvenate Cells for Tissue Engineering," *J. Tissue Eng. Regen. Med*. May 6(5):414-20.
Greene, et al., 2019, "Engineering Synthetic Chromosomes by Sequential Loading of Multiple Genomic Payloads over 100 Kilobase Pairs in Size." *Mol. Ther. Meth. & Clin. Dev*., 13:463-473.
Shitara, et al., 2008, "Telomerase-mediated life-span extension of human primary fibroblasts by human artificial chromosome (HAC) vector." Biochem. Biophys. Res. Commun. 369(3):807-11.

\* cited by examiner

BAC GENOMIC CLONE RETROFITTING AND hSynC INTEGRATION

STEP 1:
PCR amplify the recyclable attB-lox-GFP::BSR-lox with primers containing homology to the BAC/PAC vector backbone (black line)

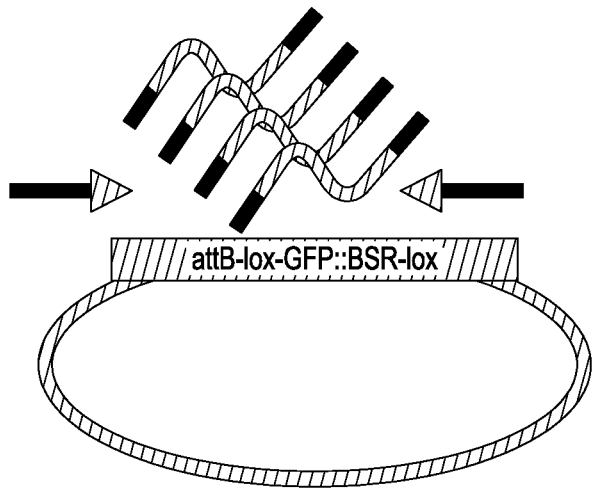

STEP 2:
Use Red/ET recombination to integrate the attB-lox-GFP::BSR-lox PCR product onto the BAC/PAC clone

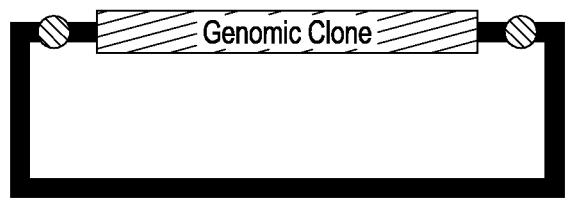

STEP 3:
Use λINTR to integrate the BAC clone into the hSynC chromosome

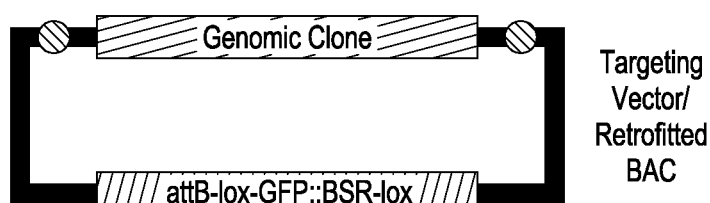

Targeting Vector/ Retrofitted BAC

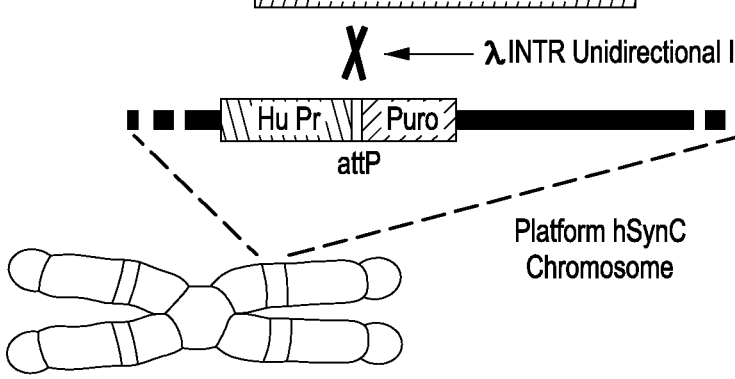

λINTR Unidirectional Integrase

Platform hSynC Chromosome

FIG. 3

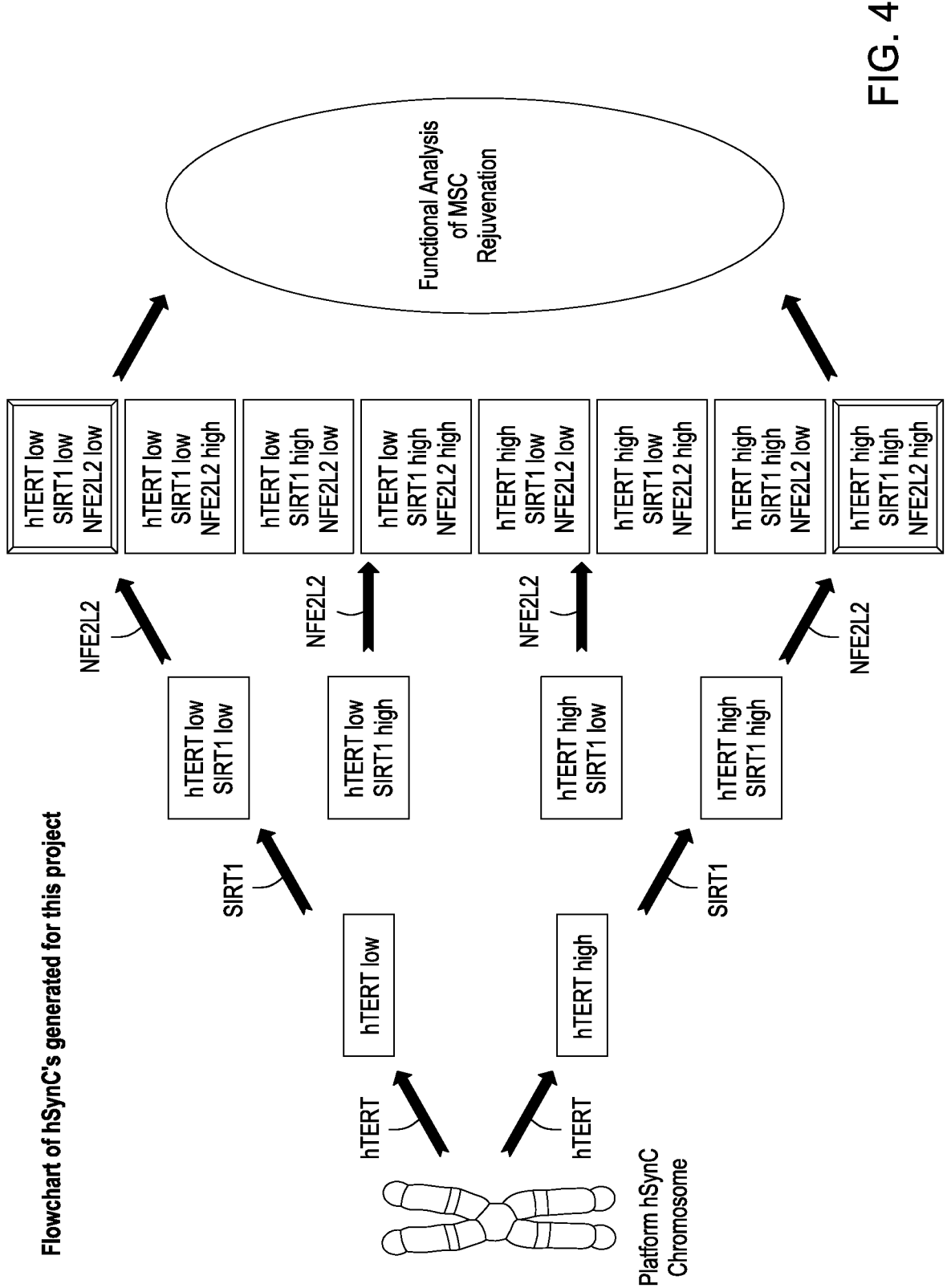

METHODS OF CELL RENEWAL

CROSS-REFERENCE TO RELATED APPLICATIONS

The present application claims priority to U.S. Provisional Patent Application No. 62/434,934, filed Dec. 15, 2016 and is incorporated here by reference.

STATEMENT REGARDING GOVERNMENT SUPPORT

This invention was made with Government support under contract D15PC00008 awarded by DARPA. The Government has certain rights in this invention.

FIELD OF THE INVENTION

The field of the invention encompasses compositions and methods to rejuvenate cells to improve the replicative and differentiation capacity thereof.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Cells are of varying replicative capacity, from those with a highly limited ability to replicate themselves, such as human diploid fibroblasts from elderly patients, to transformed cells with limitless replicative capacity such as cancer cells. The ability to provide a cell type of interest with extended replicative capacity would enable novel applications of said cells.

Stem cells are undifferentiated cells that can differentiate into more specialized cell types and divide to produce more stem cells. In mammals, there are two broad types of stem cells: embryonic stem cells, which are isolated from the inner mass of blastocysts, and adult stem cells, which are found in various tissues. In adult animals, stem cells and progenitor cells act as a repair system for the body, restoring and replenishing adult tissues as they age. There is great interest in the use of stem cells to treat or prevent diseases or other conditions. For example, bone marrow transplant has been used for many years. In yet another example, adult-derived mesenchymal stem cells (MSCs) have shown great promise for use in regenerative therapies to treat degenerative pathologies. Advantages of using MSCs for this purpose include their ready availability from the subject to be treated and the low risk of malignant transformation.

Successful use of stem cells generally requires expansion in vitro prior to transfusion; however, the requirement of expansion exposes the major limitation of the use of stem cells in regenerative medicine—their limited lifespan. Further limiting the usefulness of stem cells in autologous transplant therapy—a preferred approach to transplant therapy—is the reduced differentiation potential observed in aged stem cells relative to more youthful cells. That is, the stem cells of more elderly individuals—the individuals who are most likely to need regenerative therapies—have less differentiation potential, and thus these stem cells are less efficacious for treatment.

Thus, there is a need in the art for compositions and methods that allow for the rejuvenation of cells, extending both the replicative and differentiation capacity of the cells. The present invention provides methods and compositions that address this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

Thus, the present invention provides methods for improving the replicative and differentiation capacity of cells comprising: providing cells; transfecting the cells with a synthetic chromosome comprising at least one of a stably-integrated expression cassette expressing TERT, a stably-integrated expression cassette expressing SIRT1, and a stably-integrated expression cassette expressing NFE2L2; and/or expressing at least one of TERT, SIRT1, or NFE2L2, wherein expression of TERT, SIRT1, or NFE2L2 from the synthetic chromosome in the cells prolongs the replicative and differentiation capacity of the cells. In some embodiments of the methods of the invention, the synthetic chromosome comprises an expression cassette expressing TERT, and in some aspects of this embodiment, the expression vector comprises an endogenous TERT promoter whereas in other aspects, the expression vector comprises an inducible promoter. In some embodiments of the methods of the invention, the synthetic chromosome comprises an expression cassette expressing SIRT1, and in some aspects of this embodiment, the expression vector comprises an endogenous SIRT1 promoter, whereas in other aspects the expression vector comprises an inducible promoter. In yet other embodiments of the methods of the invention, the synthetic chromosome comprises an expression cassette expressing NFE2L2, and in some aspects of this embodiment, expression vector comprises an endogenous NFE2L2 promoter, whereas in other aspects, the expression vector comprises an inducible promoter. In some aspects, the synthetic chromosome is a human synthetic chromosome.

In yet other embodiments of the invention, the synthetic chromosome comprises at least two of a stably-integrated expression cassette expressing TERT, a stably-integrated expression cassette expressing SIRT1, and a stably-integrated expression cassette expressing NFE2L2, and in other embodiments, the synthetic chromosome comprises all of a stably-integrated expression cassette expressing TERT, a stably-integrated expression cassette expressing SIRT1, and a stably-integrated expression cassette expressing NFE2L2. In some aspects, one or more of TERT, SIRT1, and NFE2L2 are expressed from an endogenous promoter, and in some aspects, one or more of TERT, SIRT1, and NFE2L2 are expressed from an inducible promoter. Again, in some aspects, the synthetic chromosome is a human synthetic chromosome.

In some embodiments of the methods of the invention, the synthetic chromosome is produced via a top down approach, in other embodiments, the synthetic chromosome is produced via a bottom up approach, in yet other embodiments, the synthetic chromosome is produced via engineering of naturally occurring minichromosomes, and in yet other embodiments, the synthetic chromosome is produced via de novo chromosome generation by targeted amplification of chromosomal segments.

In some embodiments of the invention, the cells are stem cells derived from adipose tissue, in other embodiments, the stem cells are derived from bone marrow, and in yet other embodiments, the stem cells are derived from a subject to be treated. In some embodiments, the stem cells are embryonic stem cells, fetal stem cells, amniotic stem cells, adult stem cells, or induced pluripotent stem cells. In some specific embodiments, the stem cells are hMSCs. In other embodiments the cells are differentiated cells with limited replicative capacity, such as mammalian somatic cells and plant vegetative cells.

Other embodiments of the invention include a synthetic chromosome comprising at least one of a stably-integrated expression cassette expressing TERT, a stably-integrated expression cassette expressing SIRT1, and a stably-integrated expression cassette expressing NFE2L2, or at least two of a stably-integrated expression cassette expressing TERT, a stably-integrated expression cassette expressing SIRT1, and a stably-integrated expression cassette expressing NFE2L2, or all of a stably-integrated expression cassette expressing TERT, a stably-integrated expression cassette expressing SIRT1, and a stably-integrated expression cassette expressing NFE2L2. In some aspects, the synthetic chromosome is a human synthetic chromosome.

Other embodiments of the invention include a cell comprising a synthetic chromosome comprising at least one of a stably-integrated expression cassette expressing TERT, a stably-integrated expression cassette expressing SIRT1, and a stably-integrated expression cassette expressing NFE2L2, or at least two or all of a stably-integrated expression cassette expressing TERT, a stably-integrated expression cassette expressing SIRT1, and a stably-integrated expression cassette expressing NFE2L2.

These and other aspects and uses of the invention will be described in the detailed description.

DESCRIPTION OF THE FIGURES

FIG. 3 is a simplified depiction of BAC genomic clone retrofitting and hSynC integration.

FIG. 4 is a flowchart of hSynCs generated in one aspect of the invention.

DETAILED DESCRIPTION OF THE INVENTION

Figure 1:
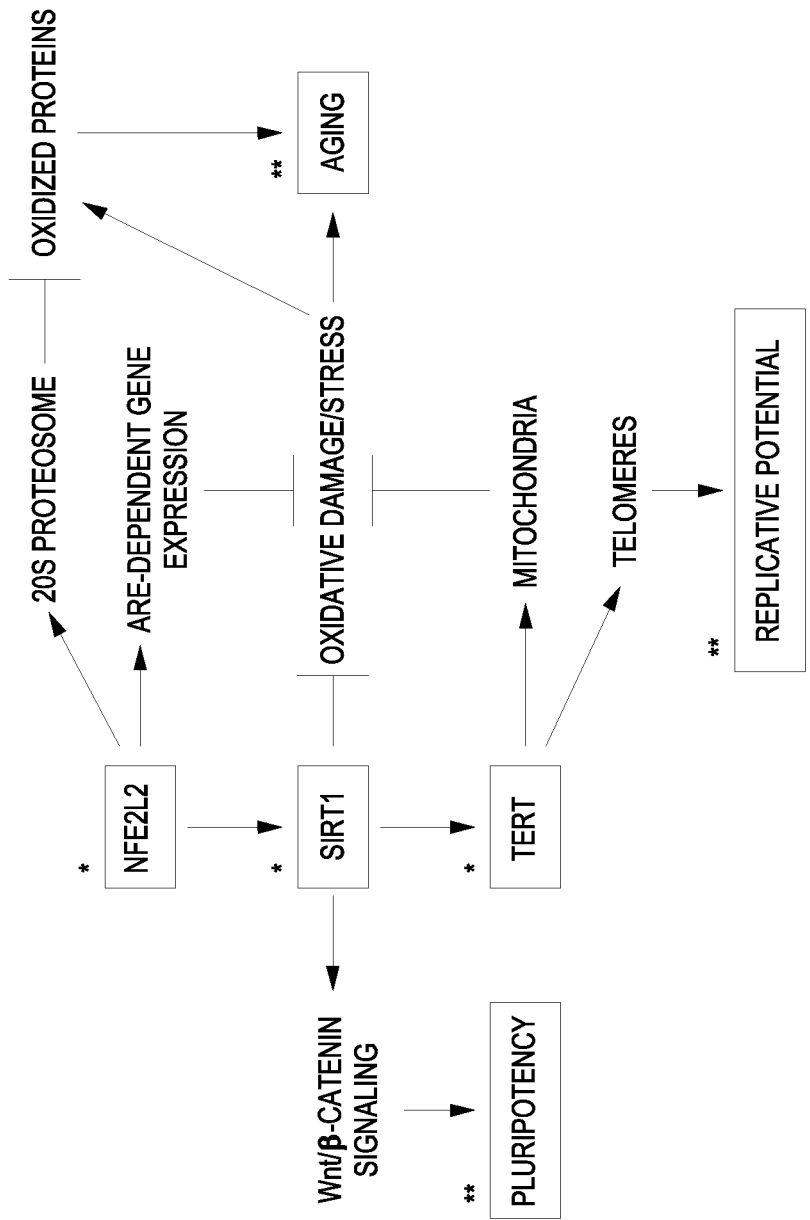
FIG. 1 is a schematic of pathways affected by TERT, SIRT1, and NFE2L2 with phenotypes.

The methods described herein may employ, unless otherwise indicated, conventional techniques and descriptions of molecular biology (including recombinant techniques), cell biology, biochemistry, and cellular engineering technology, all of which are within the skill of those who practice in the art. Such conventional techniques include oligonucleotide synthesis, hybridization and ligation of oligonucleotides, transformation and transduction of cells, engineering of recombination systems, creation of transgenic animals and plants, and human gene therapy. Specific illustrations of suitable techniques can be had by reference to the examples herein. However, equivalent conventional procedures can, of course, also be used. Such conventional techniques and descriptions can be found in standard laboratory manuals such as *Genome Analysis: A Laboratory Manual Series* (Vols. I-IV) (Green, et al., eds., 1999); *Genetic Variation: A Laboratory Manual* (Weiner, et al., eds., 2007); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); *Protein Methods* (Bollag et al., John Wiley & Sons 1996); *Nonviral Vectors for Gene Therapy* (Wagner et al. eds., Academic Press 1999); *Viral Vectors* (Kaplift & Loewy, eds., Academic Press 1995); *Immunology Methods Manual* (Lefkovits ed., Academic Press 1997); *Current Protocols in Molecular Biology* (Ausubel, et. al. eds., John Wiley & Sons, Inc.); *Current Protocols in Cell Biology* (Bonifacino, et. al. eds., John Wiley & Sons, Inc.); *Current Protocols in Cytometry* (Robinson, et. al. eds., John Wiley & Sons, Inc.); *Current Protocols in Stem Cell Biology* (Schlaeger et. al. eds., John Wiley & Sons, Inc.); *Methods in Molecular Biology Springer Protocols Series* (Walker ed., Humana Press); *Biological Aging: Methods and Protocols, Second Edition* (Tollefsbol ed., Springer, 2013); *Methods in Biological Oxidative Stress* (Henseley & Floyd, Eds, Springer, 2003); *Antibodies: A laboratory Manual, 2nd Edition* (Greenfield ed., Cold Spring Harbor Laboratory Press, 2014); *Gene Therapy Techniques, Applications and Regulations From Laboratory to Clinic* (Meager, ed., John Wiley & Sons 1999); M. Giacca, *Gene Therapy* (Springer 2010); *Gene Therapy Protocols* (LeDoux, ed., Springer 2008); *Cell and Tissue Culture: Laboratory Procedures in Biotechnology* (Doyle & Griffiths, eds., John Wiley & Sons 1998); *Mammalian Chromosome Engineering—Methods and Protocols* (G. Hadlaczky, ed., Humana Press 2011); *Essential Stem Cell Methods*, (Lanza and Klimanskaya, eds., Academic Press 2011); *Stem Cell Therapies: Opportunities for Ensuring the Quality and Safety of Clinical Offerings: Summary of a Joint Workshop* (Board on Health Sciences Policy, National Academies Press 2014); *Essentials of Stem Cell Biology*, Third Ed., (Lanza and Atala, eds., Academic Press 2013); and *Handbook of Stem Cells*, (Atala and Lanza, eds., Academic Press 2012), all of which are herein incorporated by reference in their entirety for all purposes. Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by the appended claims.

Note that as used in the present specification and in the appended claims, the singular forms "a," "and," and "the" include plural referents unless the context clearly dictates otherwise. Thus, for example, reference to "a composition" refers to one or mixtures of compositions, and reference to "an assay" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies which are described in the publication and which might be used in connection with the presently described invention.

Where a range of values is provided, it is understood that each intervening value between the upper and lower limit of that range and any other stated or intervening value in that stated range is encompassed within the invention. The upper and lower limits of these smaller ranges may independently be included in the smaller ranges, subject to any specifically excluded limit in the stated range. Where the stated range includes both of the limits, ranges excluding only one of those included limits are also included in the invention.

In the following description, numerous specific details are set forth to provide a more thorough understanding of the present invention. However, it will be apparent to one of ordinary skill in the art upon reading the specification that the present invention may be practiced without one or more of these specific details. In other instances, features and procedures well known to those skilled in the art have not been described in order to avoid obscuring the invention.

Definitions

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

As used herein, the term "adult-derived mesenchymal stem cells" ("MSCs") refers to cells that can be isolated from bone marrow, adipose tissue, peripheral blood, dental pulp, lung tissue or heart tissue from a non-fetal animal. Human MSCs are known to positively express cell surface markers CD105 (SH2), CD73 (SH3), CD44 and CD90, and do not express cell surface markers CD45, CD34, CD14, CD11b, or HLA-DR. Adult-derived mesenchymal stem cells exhibit plastic-adherence under standard culture conditions, are able to develop as fibroblast colony forming units, and are competent for in vitro differentiation into osteoblasts, chondroblasts and adipocytes. "hMSCs" as used herein refers to human adult-derived mesenchymal stem cells.

"Binding" as used herein (e.g., with reference to a nucleic acid-binding domain of a polypeptide) refers to a non-covalent interaction between a polypeptide and a nucleic acid. While in a state of non-covalent interaction, the polypeptide and nucleic acid are said to be "associated", "interacting", or "binding". Binding interactions are generally characterized by a dissociation constant (Kd) of less than $10^{-6}$ M to less than $10^{-15}$ M. "Affinity" refers to the strength of binding, increased binding affinity being correlated with a lower Kd.

By "binding domain" it is meant a polypeptide or protein domain that is able to bind non-covalently to another molecule. A binding domain can bind to, for example, a DNA molecule (a DNA-binding protein), an RNA molecule (an RNA-binding protein) and/or a protein molecule (a protein-binding protein).

A "cell" is meant to include a cell or cells from various unicellular and multicellular organisms including but not limited to humans, rodents, canines, felines, agricultural species, nematodes, insects, and fishes. In addition, a cell includes undifferentiated cells such as stem cells as well as partially- or seemingly fully-differentiated cells such as skin fibroblasts.

A "centromere" is any nucleic acid sequence that confers an ability of a chromosome to segregate to daughter cells through cell division. A centromere may confer stable segregation of a nucleic acid sequence, including a synthetic chromosome containing the centromere, through mitotic and meiotic divisions. A centromere does not necessarily need to be derived from the same species as the cells into which it is introduced, but preferably the centromere has the ability to promote DNA segregation in cells of that species. A "dicentric" chromosome is a chromosome that contains two centromeres. A "formerly dicentric chromosome" is a chromosome that is produced when a dicentric chromosome fragments. A "chromosome" is a nucleic acid molecule—and associated proteins—that is capable of replication and segregation in a cell upon division of the cell. Typically, a chromosome contains a centromeric region, replication origins, telomeric regions and a region of nucleic acid between the centromeric and telomeric regions. An "acrocentric chromosome" refers to a chromosome with arms of unequal length.

A "coding sequence" or a sequence that "encodes" a peptide is a nucleic acid molecule that is transcribed (in the case of DNA) and translated (in the case of mRNA) into a polypeptide in vivo when placed under the control of appropriate control sequences. The boundaries of the coding sequence typically are determined by a start codon at the 5' (amino) terminus and a translation stop codon at the 3' (carboxy) terminus.

The term DNA "control sequences" refers collectively to promoter sequences, polyadenylation signals, transcription termination sequences, upstream regulatory domains, origins of replication, internal ribosome entry sites, enhancers, and the like, which collectively provide for the replication, transcription and translation of a coding sequence in a recipient cell. Not all of these types of control sequences need to be present so long as a selected coding sequence is capable of being replicated, transcribed and translated in an appropriate host cell.

"Endogenous chromosomes" refer to chromosomes found in a cell prior to generation or introduction of a synthetic chromosome.

As used herein, "euchromatin" refers to chromatin that stains diffusely and that typically contains genes, and "heterochromatin" refers to chromatin that remains unusually condensed and is thought to be transcriptionally inactive. Highly repetitive DNA sequences (satellite DNA) are usually located in regions of the heterochromatin surrounding the centromere.

The terms "heterologous DNA" or "foreign DNA" (or "heterologous RNA" or "foreign RNA") are used interchangeably and refer to DNA or RNA that does not occur naturally as part of the genome in which it is present, or is found in a location or locations and/or in amounts in a genome or cell that differ from that in which it occurs in nature. Examples of heterologous DNA include, but are not limited to, DNA that encodes a gene product or gene product(s) of interest. Other examples of heterologous DNA include, but are not limited to, DNA that encodes traceable marker proteins as well as regulatory DNA sequences.

As used herein, the term "NFE2L2" refers to the human gene that encodes nuclear factor erythroid 2-related factor and variants thereof; for example, artificially-engineered and/or naturally-occurring variants of NFE2L2. "NFE2L2" refers to a transcription factor that activates antioxidant responsive element-dependent genes encoding cellular redox regulators. NFE2L2 also refers to analogous genes in other species that encode nuclear factor erythroid 2, or an analogous nuclear factor.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome), and may still have interactions resulting in altered regulation.

A "promoter" or "promoter sequence" is a DNA regulatory region capable of binding RNA polymerase in a cell and initiating transcription of a polynucleotide or polypeptide coding sequence such as messenger RNA, ribosomal RNAs, small nuclear or nucleolar RNAs or any kind of RNA transcribed by any class of any RNA polymerase I, II or III.

"Recognition sequences" are particular sequences of nucleotides that a protein, DNA, or RNA molecule, or combinations thereof (such as, but not limited to, a restriction endonuclease, a modification methylase or a recombinase) recognizes and binds. For example, a recognition sequence for Cre recombinase is a 34 base pair sequence containing two 13 base pair inverted repeats (serving as the recombinase binding sites) flanking an 8 base pair core and designated loxP (see, e.g., Sauer, Current Opinion in Biotechnology, 5:521-527 (1994)). Other examples of recognition sequences, include, but are not limited to, attB and attP, attR and attL and others that are recognized by the recombinase enzyme bacteriophage Lambda Integrase. The recombination site designated attB is an approximately 33 base pair sequence containing two 9 base pair core-type Int binding sites and a 7 base pair overlap region; attP is an approximately 240 base pair sequence containing core-type Int binding sites and arm-type Int binding sites as well as sites for auxiliary proteins IHF, FIS, and Xis (see, e.g., Landy, Current Opinion in Biotechnology, 3:699-7071 (1993)).

A "recombinase" is an enzyme that catalyzes the exchange of DNA segments at specific recombination sites. An integrase refers to a recombinase that is usually derived from viruses or transposons, as well as perhaps ancient viruses. "Recombination proteins" include excisive proteins, integrative proteins, enzymes, co-factors and associated proteins that are involved in recombination reactions using one or more recombination sites (see, Landy, Current Opinion in Biotechnology, 3:699-707 (1993)). The recombination proteins used in the methods herein can be delivered to a cell via an expression cassette on an appropriate vector, such as a plasmid, and the like. In other embodiments, recombination proteins can be delivered to a cell in protein form in the same reaction mixture used to deliver the desired nucleic acid(s). In yet other embodiments, the recombinase could also be encoded in the cell and expressed upon demand using a tightly controlled inducible promoter.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

"Ribosomal RNA" (rRNA) is the specialized RNA that forms part of the structure of a ribosome and participates in the synthesis of proteins. Ribosomal RNA is produced by transcription of genes which, in eukaryotic cells, are present in multiple copies. In human cells, the approximately 250 copies of rRNA genes (i.e., genes which encode rRNA) per haploid genome are spread out in clusters on at least five different chromosomes (chromosomes 13, 14, 15, 21 and 22). In human cells, multiple copies of the highly conserved rRNA genes are located in a tandemly arranged series of rDNA units, which are generally about 40-45 kb in length and contain a transcribed region and a nontranscribed region known as spacer (i.e., intergenic spacer) DNA which can vary in length and sequence.

As used herein the term "selectable marker" refers to a gene introduced into a cell, particularly in the context of this invention into cells in culture, which confers a trait suitable for artificial selection. General use selectable markers are well-known to those of ordinary skill in the art. In preferred embodiments, selectable markers for use in a human synthetic chromosome system should be non-immunogenic in the human and include, but are not limited to: human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in $CD34^+$ cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). Drug selectable markers such as puromycin, hygromycin, blasticidin, G418, tetracycline may also be employed. In addition, using FACs sorting, any fluorescent marker gene may be used for positive selection, as may chemiluminescent markers (e.g. Halotags), and the like.

As used here, the term "SIRT1" refers to the human gene that encodes the sirtuin 1 enzyme (herein "SIRT1"), and variants thereof; for example, artificially-engineered and/or naturally-occurring variants of SIRT1. SIRT1 is also known as NAD-dependent deacetylase sirtuin-1. Sirtuin 1 is an enzyme that deacetylates proteins that contribute to cellular regeneration. SIRT also refers to analogous genes in other species that encode the sirtuin 1 enzyme, or an analogous enzyme.

As used herein, the term "stem cells" refers to embryonic stem cells, fetal stem cells, adult stem cells, amniotic stem cells, induced pluripotent stem cells (iPS cells), or any cell capable of both self-renewal and differentiation. iPS cells are adult cells reprogrammed to exhibit pluripotent capabilities.

"Site-specific recombination" refers to site-specific recombination that is effected between two specific sites on a single nucleic acid molecule or between two different molecules that requires the presence of an exogenous protein, such as an integrase or recombinase. Certain site-specific recombination systems can be used to specifically delete, invert, or insert DNA, with the precise event controlled by the orientation of the specific sites, the specific system and the presence of accessory proteins or factors. In addition, segments of DNA can be exchanged between chromosomes (chromosome arm exchange).

"Synthetic chromosomes" (also referred to as "artificial chromosomes") are nucleic acid molecules, typically DNA, that have the capacity to accommodate and express heterologous genes and that stably replicate and segregate alongside endogenous chromosomes in cells. A "mammalian synthetic chromosome" refers to chromosomes that have an active mammalian centromere(s). A "human synthetic chromosome" refers to a chromosome that includes a centromere that functions in human cells and that preferably is produced in human cells. For exemplary artificial chromosomes, see, e.g., U.S. Pat. Nos. 8,389,802; 7,521,240; 6,025,155; 6,077,697; 5,891,691; 5,869,294; 5,721,118; 5,712,134; 5,695,967; and 5,288,625 and published International PCT application Nos, WO 97/40183 and WO 98/08964.

The terms "subject", "individual" or "patient" may be used interchangeably herein and refer to a mammal, and in some embodiments, a human.

A "telomere" is a region of repetitive nucleotide sequences—in vertebrates, TTAGGG at each end of a chromosome. Telomeres protect the chromosome from deterioration and fusion with neighboring chromosomes.

As used herein, "TERT" refers to the gene that encodes telomerase reverse transcriptase (herein "TERT"), and variants thereof from within a species or variants between species. TERT is the catalytic subunit of the enzyme telomerase, and is responsible for catalyzing the addition of nucleotides to the ends of a chromosome's telomeres, preventing degradation of the chromosomal ends following replication.

As used herein, "hTERT" refers to the gene that encodes human telomerase reverse transcriptase (herein "hTERT"), and variants thereof; for example, artificially-engineered and/or naturally-occurring variants of hTERT. hTERT is the catalytic subunit of the enzyme telomerase, and is responsible for catalyzing the addition of nucleotides in a TTAGGG sequence to the ends of a chromosome's telomeres, preventing degradation of the chromosomal ends following replication.

A "vector" is a replicon, such as plasmid, phage, viral construct, cosmid, bacterial artificial chromosome, P-1 derived artificial chromosome or yeast artificial chromosome to which another DNA segment may be attached. In some instances a vector may be a chromosome such as in the case of an arm exchange from one endogenous chromosome engineered to comprise a recombination site to a synthetic chromosome. Vectors are used to transduce and express a DNA segment in cell.

The Invention

The present invention encompasses compositions and methods to rejuvenate cells for use in regenerative therapies and/or as research tools. That is, the methods and compositions of the present invention increase the replicative capacity and differentiation capacity and plasticity of cells. One embodiment of the present invention provides mammalian synthetic chromosomes—preferably human synthetic chromosomes—engineered to express TERT and/or SIRT1 and/or NFE2L2 in stem cells, particularly autologous stem cells of a subject to be treated.

For example, adult-derived mesenchymal stem cells (MSCs) have shown great promise for regenerative therapy of numerous age-associated pathologies as well as in damaged tissues and organs. Successful therapy with MSCs generally requires expansion in vitro prior to transfusion, which exposes the major weakness to the use of autologous MSCs—and all stem cells—in regenerative medicine, replicative senescence. The cap on the total number of cell divisions achievable-ranging from 20 to 40 divisions—limits the total number of cells that can be obtained. Further limiting the usefulness of stem cells in autologous transplant therapy is the reduced differentiation potential observed in aged stem cells relative to more youthful cells. Moreover, as cells age they express fewer homing receptors and have a slower doubling time, both of which impact the efficacy of cell-based therapies with older donor cells. Strategies that rejuvenate cells, extending both proliferation and differentiation capacity, greatly enhance the usefulness of these cells in regenerative medicine.

The action of adult cells is critical for tissue homeostasis; however, there is a functional decline in cells during aging and accumulation of tissue and organ damage is a major health burden in aged populations. For example, advantages of MSCs include their pluripotent nature, as they are able to differentiate into numerous cell types including connective tissue (chondrocytes, osteoblasts, adipocytes, etc.), endothelial cells and nonmesodermal cells such as neurons. In addition, MSCs are readily available and protocols to obtain MSCs from mesodermally derived tissues, such as adipose, are well developed. Thus, MSCs are a useful source of cells for autologous transplantation, limiting the need for tissue matching because each patient can be their own donor. Finally, MSCs have a low risk of malignant transformation due to their limited proliferative potential.

Aging is a result of the accumulation of damage resulting from exposure to multiple stressors. Numerous pathways have been implicated in aging. One of the best studied is the loss of specialized chromosome ends, telomeres, that occurs as a result of DNA replication and ultimately leads to uncapped chromosome ends that act as double-stranded DNA breaks. This damage can be overcome by ectopic expression of telomerase (hTERT) in many human cell types, and TERT in other animals, and in plants, fungi, etc.

Pathways affecting the redox potential of cells have also been shown to be important in aging. Accumulation of oxidative damage to protein, lipid and nucleic acid components of cells occurs as a result of exposure to reactive oxygen species. Wnt1/β-catenin signaling, as well as signaling through the p53 and and INK4a/ARF pathways, are important in transducing damage signals to elicit a senescent response. SIRT1 and NFE2L2 both play a role in the cellular response to oxidative damage. Key enzymes in the biosynthesis of NAD+(i.e., Nampt) have been shown to increase lifespan when overexpressed, likely through a SIRT1-dependent mechanism, with SIRT1 itself being NAD+ dependent. The NFE2L2-regulated gene, heme oxygenase 1, is a key player in the cellular anti-oxidant pathway. NFE2L2 also regulates the activity of the 20S proteasome. Removal of oxidized proteins via the 20S proteasome is important to counteract accumulation of damage; pathways regulating the effectiveness of the 20S proteasome have been implicated in delaying aging phenotypes.

Inflammation is associated with aging via key mediators of the senescence-associated secretory phenotype, IL-6 and IL-8. Klotho interacts with retinoic acid-inducible gene-1 (RIG-1) to inhibit RIG-1 dependent expression of IL-6 and IL-8, thereby delaying aging. In addition, evidence suggests that Klotho may delay aging by inhibiting the p53 DNA damage pathway. Peroxisome proliferator-activated receptors gamma and delta are transcription factors that play a key role in the anti-oxidant and anti-inflammatory cellular responses through activation of downstream gene expression including expression of Klotho. Crosstalk between these pathways leads to a complicated network of cellular factors contributing to cellular responses to limit damage and subsequent aging.

More general and poorly understood changes in global gene expression as a result of changes in chromatin conformation—through changes in expression in DNA methyltransferases, histone deacetylases and the non-histone high mobility group protein A2—have also been reported during aging. Changes in nuclear architecture also occurs through alterations in maturation of nuclear lamin A from the prelamin A precursor. Genes affected by these processes include some of those discussed above as well as genes still to be identified.

Aging of somatic cells, including stem cells generally, is driven in part through attrition of chromosome ends, e.g., telomeres, as a consequence of imperfect end-replication and end-processing reactions. Germline and stem cells overcome these issues through the action of the specialized reverse transcriptase, telomerase, which adds DNA de novo to chromosome ends. However, numerous studies have shown that telomerase in stem cells is not sufficient to completely overcome telomere loss, ultimately limiting the number of divisions stem cells can undergo. Both differentiation potential and regenerative capacity of bone-marrow derived stem cells are reduced following serial transplantation; similarly, it has been demonstrated that telomeres are shorter in human allogeneic transplant recipients than in their respective donors, and both proliferative capacity and differentiation potential of circulating myeloid cells was significantly reduced in recipients as compared to their respective donors. Further, in addition to its essential role at chromosome ends, telomerase may also play a role in responding to oxidative stress. Production of reactive oxygen species increases as cells age—likely as a result of mitochondrial damage—and oxidative damage is thought to be a major driver of aging. In recent years it has been demonstrated that telomerase relocates to mitochondria when the cell is under oxidative stress, and increasing evidence suggests that relocation of the catalytic subunit of human telomerase, hTERT, to the mitochondria is essential in limiting oxidative damage. Damaged mitochondria result in higher production of reactive oxygen species leading to a dangerous cycle of ever increasing oxidative damage.

Additionally, expression of SIRT1, an NAD+-dependent protein deacetylase, is decreased in aged stem cells and it has been found that forced ectopic expression of SIRT1 can delay senescence of stem cells. SIRT1 has been shown to regulate oxidative stress and mediate the longevity effected by caloric restriction, and has also been shown to regulate Wnt/β-catenin signaling that is important in the maintenance of stem cell pluripotency. Importantly, SIRT1 affects replicative senescence via upregulation of hTERT, thereby limiting oxidative damage to telomeres and mitochondria resulting in an extension of cellular replicative lifespan.

Nuclear factor erythroid 2-related factor (NFE2L2), a master regulator of the cellular oxidative stress response, is a transcription factor that activates antioxidant responsive element (ARE)-dependent genes encoding cellular redox regulators. In the absence of oxidative stress, NFE2L2 is bound to its inhibitor KEAP1 and targeted for proteasome mediated degradation. In the presence of stress, NFE2L2 is released from this complex and translocates to the nucleus to activate genes involved in the antioxidant response. NFE2L2 also positively regulates SIRT1 mRNA and protein through negative regulation of p53. In addition, NFE2L2 activates expression of subunits of the 20S proteasome. Aged cells contain high levels of oxidized proteins that can form aggregates resistant to degradation. Activation of the 20S proteasome via NFE2L2-dependent gene expression has also been found to result in extension of lifespan and stemness, presumably through proteasome-dependent degradation of oxidized proteins. Given the role of NFE2L2 in multiple pathways it is not surprising that forced expression of NFE2L2 results in improved differentiation potential and maintenance of stemness in stem cells.

As discussed, a major challenge to the use of stem cells in cell-based regenerative medicine—particularly for use in autologous transplantation for age-associated degenerative conditions such as osteoarthritis—is the limited lifespan and loss of differentiation potential that accompanies aging. The present invention provides compositions and methods for expressing TERT, SIRT1, and/or NFE2L2 in stem cells. Aging is regulated via a series of interrelated pathways. In humans, expression of hTERT, SIRT1 and NFE2L2—all of which have been demonstrated to extend lifespan through interactive pathways regulating telomere damage and oxidative stress (see FIG. 1)—are excellent targets for manipulation for rejuvenating stem cells. However, the primary roadblock to polygenic engineering is the limited capacity of current vectors and the requirement for serial rounds of transfection or transduction to load all the required elements into the target cell. In addition, a major risk associated with genetically altering cells to ectopically express these genes using standard engineering vectors is elimination of an intrinsic tumor suppressor mechanism via stable integration into the genome. Since inception over three decades ago, progress in bioengineering of cells has been held back by the absence of the one tool required to address complex polygenicity and/or delivery of large genetic payloads: a stable, non-integrating, self-replicating and biocompatible intracellular platform that ensures controlled expression. The engineered synthetic chromosomes of the present invention provide the breakthrough in biological bandwidth required to manage complex polygenic challenges and introduction of large genetic payloads.

Stem Cells Generally

Stem cells possess two properties: self-renewal—the ability to go through numerous cycles of cell division while maintaining a non-differentiated state—and potency—the capacity to differentiate into specialized cell types. Stem cells can be totipotent, which is the potential to make all cell types; pluripotent, which is the potential to make all cell types apart from gametes; multipotent, which is the potential to make some cell types; oligopotent, which is the potential to differentiate into only a few cell types; or unipotent, which is the potential to differentiate into a single cell type while retaining the property of self-renewal. In practice, stem cells are identified by whether they can regenerate tissue.

Embryonic stem cells are the cells of the inner cell mass of a blastocyst, a stage of an embryo typically reached within 4-5 days post fertilization in humans. Embryonic stem cells are pluripotent. Adult stem cells are found in post-embryonic animals. Pluripotent adult stem cells are rare and generally small in number, but can be found in umbilical cord blood, bone marrow, adipose tissue, blood and other tissues. Most adult stem cells are lineage-restricted (multipotent) and are generally referred to by their tissue of origin (e.g., mesenchymal, adipose-derived, endothelial, etc.) Induced pluripotent stem cells are adult, non-stem cells that have been reprogrammed to give rise to multipotent or pluripotent cells through the use of various transcription factors.

Adult-Derived Mesenchymal Stem Cells

Adult-derived mesenchymal stem cells have been isolated from a number of different sources, including bone marrow, adipose tissue, peripheral blood, the lung and the heart. Bone marrow MSCs are isolated from bone marrow aspirate, which is a painful procedure and is accompanied by the risk of infection. The common method for generation of MSCs from bone marrow is density gradient centrifugation. The collected fraction containing mononuclear cells is washed and the cells are seeded on a plastic tissue culture dish for proliferation. Adipose-derived MSCs are usually isolated from the biological material generated during liposuction, lipoplasty, or lipectomy procedures by enzymatic digestion with collagenase followed by centrifugation and washing. Peripheral blood MSCs can be obtained from the lymphocyte separation fluid fraction of mononuclear cells after a density gradient centrifugation. The amount of MSCs that can be obtained by these isolation methods vary enormously. For example, from 1 g of adipose tissue $5\times10^3$ MSCs can be isolated, which is 500 times more cells than from an equivalent amount of bone marrow.

Synthetic Chromosome Producing Cells

The synthetic chromosomes expressing TERT and/or SIRT1 and/or NFE2L2 of the present invention are produced in cell lines in vitro before being used to transform cells, preferentially human stem cell lines. In some embodiments, the cells to be engineered to produce the synthetic chromosomes can be cells that naturally occur in a subject (human patient) in which the genes or regulatory sequences from the synthetic chromosome will ultimately be expressed. Such cells can be primary-culture cell lines established for the purpose of synthetic chromosome production specific for an individual. In other embodiments, the cells to be engineered and/or produce the synthetic chromosome are from an established cell line. A wide variety of cell lines for tissue culture are known in the art. Examples of cell lines include but are not limited to human cells lines such as 293-T (embryonic kidney), 721 (melanoma), A2780 (ovary), A172 (glioblastoma), A253 (carcinoma), A431 (epithelium), A549 (carcinoma), BCP-1 (lymphoma), BEAS-2B (lung), BR 293 (breast), BxPC3 (pancreatic carcinoma), Cal-27 (tongue), COR-L23 (lung), COV-434 (ovary), CML T1 (leukemia), DUI45 (prostate), DuCaP (prostate), FM3 (lymph node), H1299 (lung), H69 (lung), HCA2 (fibroblast), HEK0293 (embryonic kidney), HeLa (cervix), HL-60 (myeloblast), HMEC (epithelium), HT-29 (colon), HUVEC (umbilical vein epithelium), Jurkat (T cell leukemia), JY (lymphoblastoid), K562 (lymphoblastoid), KBM-7 (lymphoblastoid), Ku812 (lymphoblastoid), KCL22 (lymphoblastoid), KGI (lymphoblastoid), KYO1 (lymphoblastoid), LNCap (prostate), Ma-Me1 (melanoma), MCF-7 (mammary gland), MDF-10A (mammary gland), MDA-MB-231, -468 and -435 (breast), MG63 (osteosarcoma), MOR/0.2R (lung), MONO-MAC6 (white blood cells), MRC5 (lung), NCI-H69 (lung), NALM-1 (peripheral blood), NW-145 (melanoma), OPCN/OPCT (prostate), Peer (leukemia), Raji (B lymphoma), Saos-2 (osteosarcoma), Sf21 (ovary), Sf9 (ovary), SiHa (cervical cancer), SKBR3 (breast carcinoma), SKOV-2 (ovary carcinoma), T-47D (mammary gland), T84 (lung), U373 (glioblastoma), U87 (glioblastoma), U937 (lymphoma), VCaP (prostate), WM39 (skin), WT-49 (lymphoblastoid), and YAR (B cell). In some embodiments non-human cell lines may be employed. Rodent cell lines of interest include but are not limited to 3T3 (mouse fibroblast), 4T1 (mouse mammary), 9L (rat glioblastoma), A20 (mouse lymphoma), ALC (mouse bone marrow), B16 (mouse melanoma), B35 (rat neuroblastoma), bEnd.3 (mouse brain), C2C12 (mouse myoblast), C6 (rat glioma), CGR8 (mouse embryonic), CT26 (mouse carcinoma), E14Tg2a (mouse embryo), EL4 mouse leukemia), EMT6/AR1 (mouse mammary), Hepa1c1c7 (mouse hepatoma), J558L (mouse myeloma), MC-38 (mouse adenocarcinoma), MTD-1A (mouse epithelium), RBL (rat leukemia), RenCa (mouse carcinoma), X63 (mouse lymphoma), YAC-1 (mouse Be cell), BHK-1 (hamster kidney), and CHO (hamster ovary). In addition, embryonic cell lines; pluripotent cell lines; adult derived stem cells; reprogrammed cell lines; generic animal cell lines of any species or broadly embryonic or reprogrammed cells; primary dog cells; primary horse cells; chicken DT40 cells; dog cell lines; cat cell lines; patient autologous cell lines; and, in some preferred embodiments, the HT1080 human cell line can be utilized. Potential cells for use include any mammalian cell, but those from humans are specifically and preferentially contemplated. These cell lines and others are available from a variety of sources known to those with skill in the art (see, e.g., the American Type Culture Collection (ATCC) (Manassas, Va.)). The synthetic chromosome producing cell line can then be maintained in culture, or alternatively, the synthetic chromosome(s) can be isolated from the synthetic chromosome producing cell line and transfected into a different cell line for maintenance before ultimately being transfected into a target cell.

Synthetic Chromosome Production

The engineering of cells to improve their replicative and differentiation capacity can be accomplished by expressing TERT and/or SIRT1 and/or NFE2L2 from synthetic chromosomes produced by any method currently employed in the art. That is, the synthetic chromosomes of the present invention may be accomplished by any of the "top down", "bottom up", engineering of minichromosomes, and induced de novo chromosome generation methods used in the art. The "bottom up" approach of synthetic chromosome formation relies on cell-mediated de novo chromosome formation following transfection of a permissive cell line with cloned α-satellite sequences, which comprise typical host cell-appropriate centromeres and selectable marker gene(s), with or without telomeric and genomic DNA. (For protocols and a detailed description of these methods see, e.g., Harrington, et al., Nat. Genet., 15:345-55 (1997); Ikeno, et al., Nat. Biotechnol., 16:431-39 (1998); Masumoto, et al., Chromosoma, 107:406-16 (1998), Ebersole, et al., Hum. Mol. Gene., 9:1623-31 (2000); Henning, et al., PNAS USA, 96:592-97 (1999); Grimes, et al., EMBO Rep. 2:910-14 (2001); Mejia, et al., Genomics, 79:297-304 (2002); and Grimes, et al., Mol. Ther., 5:798-805 (2002).) Both synthetic and naturally occurring α-satellite arrays, cloned into yeast artificial chromosomes, bacterial artificial chromosomes or P1-derived artificial chromosome vectors have been used in the art for de novo synthetic chromosome formation. The products of bottom up assembly can be linear or circular, comprise simplified and/or concatamerized input DNA with an α-satellite DNA based centromere, and typically range between 1 and 10 Mb in size. Bottom up-derived synthetic chromosomes also are engineered to incorporate nucleic acid sequences that permit site-specific integration of target DNA sequence onto the synthetic chromosome.

The "top down" approach of producing synthetic chromosomes involves sequential rounds of random and/or targeted truncation of pre-existing chromosome arms to result in a pared down synthetic chromosome comprising a centromere, telomeres, and DNA replication origins. (For protocols and a detailed description of these methods see, e.g., Heller, et al., PNAS USA, 93:7125-30 (1996); Saffery, et al., PNAS USA, 98:5705-10 (2001); Choo, Trends Mol. Med., 7:235-37 (2001); Barnett, et al., Nuc. Ac. Res., 21:27-36 (1993); Farr, et al., PNAS USA, 88:7006-10 (1991); and Katoh, et al., Biochem. Biophys. Res. Commun., 321:280-90 (2004).) "Top down" synthetic chromosomes are constructed optimally to be devoid of naturally-occurring expressed genes and are engineered to contain DNA sequences that permit site-specific integration of target DNA sequences onto the truncated chromosome, mediated, e.g., by site-specific DNA integrases.

A third method of producing synthetic chromosomes known in the art is engineering of naturally occurring minichromosomes. This production method typically involves irradiation-induced fragmentation of a chromosome containing a functional, e.g., human neocentromere possessing centromere function yet lacking α-satellite DNA sequences and engineered to be devoid of non-essential DNA. (For protocols and a detailed description of these methods see, e.g., Auriche, et al., EMBO Rep. 2:102-07 (2001); Moralli, et al., Cytogenet. Cell Genet., 94:113-20 (2001); and Carine, et a., Somat. Cell Mol. Genet., 15:445-460 (1989).) As with other methods for generating synthetic chromosomes, engineered minichromosomes can be engineered to contain DNA sequences that permit site-specific integration of target DNA sequences.

The fourth approach for production of synthetic chromosomes involves induced de novo chromosome generation by targeted amplification of specific chromosomal segments. This approach involves large-scale amplification of pericentromeric/ribosomal DNA regions situated on acrocentric chromosomes. The amplification is triggered by co-transfection of excess DNA specific to the pericentric region of chromosomes, such as ribosomal RNA, along with DNA sequences that allow for site-specific integration of target DNA sequences and also a drug selectable marker which integrates into the pericentric regions of the chromosomes. (For protocols and a detailed description of these methods see, e.g., Csonka, et al., J. Cell Sci 113:3207-16 (2002); Hadlaczky, et al., Curr. Opini. Mol. Ther., 3:125-32 (2001); and Lindenbaum and Perkins, et al., Nuc. Ac. Res., 32(21): e172 (2004).) During this process, targeting to the pericentric regions of acrocentric chromosomes with co-transfected DNA induces large-scale chromosomal DNA amplification, duplication/activation of centromere sequences, and subsequent breakage and resolution of dicentric chromosomes resulting in a "break-off" satellite DNA-based synthetic chromosome containing multiple site-specific integration sites.

The vectors carrying the components appropriate for synthetic chromosome production can be delivered to the cells to produce the synthetic chromosome by any method known in the art. The terms transfection and transformation refer to the taking up of exogenous nucleic acid, e.g., an expression vector, by a host cell whether or not any coding sequences are, in fact, expressed. Numerous methods of transfection are known to the ordinarily skilled artisan, for example, by *Agrobacterium*-mediated transformation, protoplast transformation (including polyethylene glycol (PEG)-mediated transformation, electroporation, protoplast fusion, and microcell fusion), lipid-mediated delivery, liposomes, electroporation, sonoporation, microinjection, particle bombardment and silicon carbide whisker-mediated transformation and combinations thereof (see, e.g., Paszkowski, et al., EMBO J., 3:2717-2722 (1984); Potrykus, et al., Mol. Gen. Genet., 199:169-177 (1985); Reich, et al., Biotechnology, 4:1001-1004 (1986); Klein, et al., Nature, 327:70-73 (1987); U.S. Pat. No. 6,143,949; Paszkowski, et al., in *Cell Culture and Somatic Cell Genetics of Plants*, Vol. 6, Molecular Biology of Plant Nuclear Genes, (Schell and Vasil, eds., Academic Publishers 1989); and Frame, et al., Plant J., 6:941-948 (1994)); direct uptake using calcium phosphate (Wigler, et al., Proc. Natl. Acad. Sci. U.S.A., 76:1373-1376 (1979)); polyethylene glycol (PEG)-mediated DNA uptake; lipofection (see, e.g., Strauss, Meth. Mol. Biol., 54:307-327 (1996)); microcell fusion (Lambert, Proc. Natl. Acad. Sci. U.S.A., 88:5907-5911 (1991); U.S. Pat. No. 5,396,767; Sawford, et al., Somatic Cell Mol. Genet., 13:279-284 (1987); Dhar, et al., Somatic Cell Mol. Genet., 10:547-559 (1984); and McNeill-Killary, et al., Meth. Enzymol., 254:133-152 (1995)); lipid-mediated carrier systems (see, e.g., Teifel, et al., Biotechniques, 19:79-80 (1995); Albrecht, et al., Ann. Hematol., 72:73-79 (1996); Holmen, et al., In Vitro Cell Dev. Biol. Anim., 31:347-351 (1995); Remy, et al., Bioconjug. Chem., 5:647-654 (1994); Le Bolch, et al., Tetrahedron Lett., 36:6681-6684 (1995); and Loeffler, et al., Meth. Enzymol., 217:599-618 (1993)); or other suitable methods. Methods for delivery of synthetic chromosomes also are described in U.S. application Ser. No. 09/815,979. Successful transfection is generally recognized by detection of the presence of the heterologous nucleic acid within the transfected cell, such as, for example, any visualization of the heterologous nucleic acid, expression of a selectable marker or any indication of the operation of a vector within the host cell. For a description of delivery methods useful in practicing the present invention, see U.S. Pat. Nos. 5,011,776; 5,747,308; 4,966,843; 5,627,059; 5,681,713; Kim and Eberwine, Anal. Bioanal. Chem. 397 (8): 3173-3178 (2010).

The choice of vector to be used in delivery of the components of the synthetic chromosomes including the TERT, SIRT1, and NFE2L2 expression vectors will depend upon a variety of factors such as the type of cell in which propagation is desired. Certain vectors are useful for amplifying and making large amounts of the desired DNA sequence, while other vectors are suitable for expression in cells in culture. The choice of appropriate vector is well within the skill of those in the art, and many vectors are available commercially. To prepare the constructs, a polynucleotide is inserted into a vector, typically by means of ligation of a sequence into a cleaved restriction enzyme site in the vector. Alternatively, the desired nucleotide sequence (e.g., TERT and/or SIRT1 and/or NFE2L2) can be inserted by homologous recombination or site-specific recombination. Typically homologous recombination is accomplished by attaching regions of homology (e.g., cre-lox, att sites, etc.) to the vector on the flanks of the desired nucleotide sequence. Nucleic acids containing such sequences can be added by, for example, ligation of oligonucleotides, or by polymerase chain reaction using primers comprising both the region of homology and a portion of the desired nucleotide sequence. Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Additional vectors include bacterial artificial chromosomes (BACs) based on a functional fertility plasmid (F-plasmid), yeast artificial chromosomes (YACs), and P1-derived artificial chromosomes, DNA constructs derived from the DNA of P1 bacteriophage (PACS). Alternatively and preferably, recombinant virus vectors may be engineered, including but not limited to those derived from viruses such as herpes virus, retroviruses, vaccinia virus, poxviruses, adenoviruses, lentiviruses, adeno-associated viruses or bovine papilloma virus.

Artificial Chromosome Systems

An artificial chromosome expression system (ACE system) has been described previously as a means to introduce large payloads of genetic information into the cell (Lindenbaum and Perkins, et al., Nuc. Ac. Res., 32(21):e172 (2004); Perkins et al., Chromosome-based platforms, USA, Chromos Molecular Systems (2006); Perkins et al., Chromosome-based platforms, USA, Chromos Molecular Systems (2003), and Perkins, et al., Chromosome-based platforms, USA, Chromos Molecular Systems (2005)). The ACE System consists of a platform chromosome (ACE chromosome) containing approximately 75 site-specific, recombination acceptor sites that can carry single or multiple copies of genes of interest using specially designed ACE targeting vectors (pAPP) and a site-specific integrase (ACE Integrase; see FIG. 2). The ACE Integrase is a derivative of the bacteriophage lambda integrase (INT) engineered to direct site-specific unidirectional recombination in mammalian cells in lieu of bacterial encoded, host integration accessory factors (λINTR). The transfer of an ACE chromosome carrying multiple copies of a red fluorescent protein reporter gene into human MSCs has been demonstrated (see Lindenbaum and Perkins, et al., Nuc. Ac. Res., 32(21):e172 (2004)) (See FIG. 2). Fluorescent in situ hybridization and fluorescent microscopy demonstrated that the ACEs were stably maintained as single chromosomes and expression of transgenes in both MSCs and differentiated cell types is maintained (Vanderbyl et al., Stem Cells, 22:324-33 (2004)). A humanized version of the ACE system, termed hSynC, is used to express hTERT and/or SIRT1 and/or NFE2L2 in the cells, particularly human stem cells.

Figure 2:
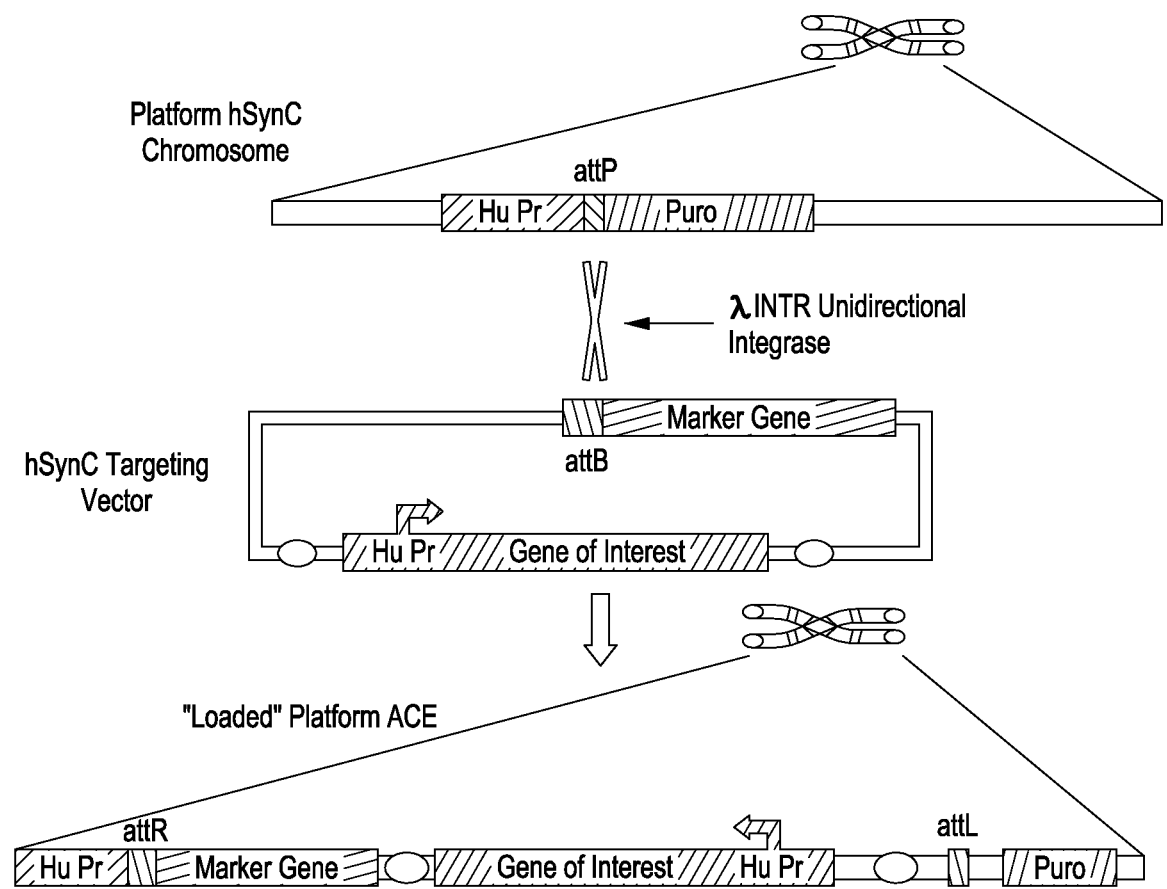
FIG. 2 is a simplified depiction of the platform synthetic chromosome and targeting vector system.

The hSynC system comprises a human platform chromosome (hSynC) containing multiple site-specific, recombination acceptor sites that can carry single or multiple copies of genes of interest using specially designed targeting vectors (pAPP) and the site-specific λ integrase (FIG. 2). The transfer of a murine derived ACE chromosome carrying multiple copies of a red fluorescent protein reporter gene into human MSCs has been demonstrated (Lindenbaum et al., Nucleic Acid Res., 32, e172 (2004); FIG. 2). Fluorescent in situ hybridization and fluorescent microscopy demonstrated that the ACEs were stably maintained as single chromosomes and expression of transgenes in both MSCs and differentiated cell types is maintained (Vanderbyl et al., Stem Cells, 22:324-33 (2004)).

hTERT, SIRT1, and NFE2L2 Expression Cassettes

The hTERT gene, located on the short arm of chromosome 5 at 5p15.33 in humans, is >40 kb in length, which limits introduction of the gene and its associated regulatory systems using conventional gene transfer technologies. However, large genetic payloads are easily incorporated into synthetic chromosomes. BAC clones spanning the hTERT locus have been identified and characterized. The most widely used clone, RP11-117B23, is about 160 kb in length and has been demonstrated to recapitulate in vivo regulation of hTERT in development and tumorigenesis. An alternative 54 kb BAC containing the entire hTERT locus and flanking sequences (11 kb 5' and 1.2 kb 3' of the hTERT coding region) has also been characterized. Species appropriate transcriptional regulation of the hTERT gene was retained when this BAC was introduced into mice.

SIRT1 is an NAD+ dependent protein deacetylase that has been demonstrated to play a role in aging, including aging of stem cells. In humans, SIRT1 is located on the long arm of chromosome 10 at 10q21.3 and is over 33 kb in length including the promoter region which is located within 1.2 kb of the first exon. SIRT1 flanking genes include an U6 small nuclear RNA pseudogene 25 kb upstream and a DNAJ homolog C12 a further 12 kb centromeric to the SIRT1 start site. HERC4, encoding a probable ubiquitin-protein ligase, is located only 3 kb telomeric to the end of the SIRT1 coding region. No BACs spanning the region have been functionally characterized in the literature; however, two BACs spanning the region and portions of flanking genes are available from the Roswell Park Cancer Institute Human Male BAC library (RPCI-11) through Empire Genomics (Buffalo, N.Y.). RP11-22C9 is 160 kb in length and contains approximately 20 kb of upstream flanking sequences as well as 68% of the HERC4 locus. RP11-867F19 is 177 kb in length and contains 56% of the HERC4 locus and 27% of the DNAJC12 locus. The experiments detailed below utilize the RP11-22C9 BAC because it does not contain full length copies of either of the flanking genes.

The NFE2L2 gene, which in humans is located on the long arm of chromosome 2 at 2q31.2, has several transcript variants, the largest of which is over 160 kb in length. The ability to transfer large genetic payloads using the synthetic chromosomes of the present invention make this the only currently feasible technology to introduce the entire locus. The proximal promoter region of NFE2L2 contains ARE elements and is subject to epigenetic regulation through CpG methylation. Flanking genes include alkylglycerone phosphate synthase, which catalyzes the second step of ether lipid biosynthesis in the peroxisome, and lies 50 bp upstream from the start of the largest NFE2L2 transcript variant and heterogeneous nuclear ribonucleoprotein A3, involved in cytoplasmic trafficking of RNAs and pre-mRNA splicing, 10 kb downstream from the last exon of NFE2L2. Several non-coding RNAs are also located between the start of the gene and the fifth exon of the largest transcript variant. The BAC clone RP11-844A8 is over 180 kb in length and spans the entire NFE2L2 locus including non-coding RNAs but contains only 7% and 29% of the flanking loci, respectively.

In one embodiment, the hTERT, SIRT1, NFE2L2 or combination hTERT/SIRT1/NFE2L2 expression vectors of the present invention that are inserted into human synthetic chromosomes provide transcriptional and translational regulatory sequences, and in some embodiments provide for either inducible or constitutive expression, where the hTERT, SIRT1, and/or NFE2L2 coding regions are operably linked under the transcriptional control of the transcriptional initiation region and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences.

Expression of hTERT is controlled at multiple levels, including transcription, alternative splicing and post-translational mechanisms; however, transcription of hTERT as regulated through its promoter elements is believed to be the most important regulatory mechanism. The hTERT promoter does not have either TATA or CAAT boxes and the promoter bridges both upstream sequences and downstream exonic sequences. The methods and compositions of the present invention include inserting hTERT into the human artificial chromosome under the control of endogenous regulatory elements in some aspects and under the control of inducible promoter systems in alternative aspects. The benefit to using hTERT endogenous regulatory sequences is that expression of hTERT undergoes age-associated epigenetic reprogramming to naturally control expression; thus, in this aspect, the stem cells naturally reach senescence. Similarly, the methods and compositions of the present invention include inserting SIRT1, and/or NFE2L2 into the human artificial chromosome under the control of endogenous regulatory elements in some aspects and under the control of an inducible promoter system in alternative aspects.

In general, the inducible promoters of use in the present invention are not limited, as long as the promoter is capable of inducing expression of the downstream gene in response to an external stimulus. One such system involves tetracycline-controlled transcriptional activation where transcription is reversibly turned on (Tet-On) or off (Tet-Off) in the presence of the antibiotic tetracycline or a derivative thereof, such as doxycycline. In a Tet-Off system, expression of tetracycline response element-controlled genes can be repressed by tetracycline and its derivatives. Tetracycline binds the tetracycline transactivator protein, rendering it incapable of binding to the tetracycline response element sequences, preventing transactivation of tetracycline response element-controlled genes. In a Tet-On system on the other hand, the tetracycline transactivator protein is capable of initiating expression only if bound by tetracycline; thus, introduction of tetracycline or doxycycline initiates the transcription of hTERT and/or SIRT1 and/or NFE2L2. Another inducible promoter system known in the art is the estrogen receptor conditional gene expression system. Compared to the Tet system, the estrogen receptor system is not as tightly controlled; however, because the Tet system depends on transcription and subsequent translation of a target gene, the Tet system is not as fast-acting as the estrogen receptor system. Alternatively, a Cumate Switch Inducible expression system—in the repressor configuration—may be employed. The Cumate Switch Inducible expression system is based on the bacterial repressor controlling the degradative pathway for p-cymene in *Pseudomonas putida*. High levels of the reaction product, p-cumate, allow binding of the repressor CymR to the operator sequences (CmO) of the p-cym and p-cmt operon.

Transforming the Stem Cells

To date, isolation and transfer of synthetic chromosomes including human synthetic chromosomes has involved utilizing microcell mediated cell transfer (MMCT) technology or dye-dependent chromosome staining with subsequent flow cytometric-based sorting. In the MMCT technique, donor cells are chemically induced to multinucleate their chromosomes with subsequent packaging into microcells and eventual fusion into recipient cells. The establishment of transferred chromosomes in the recipient cells is carried out with drug selection and intact delivery of the transferred chromosome confirmed by FISH. For flow cytometric-based transfer, mitotically arrested chromosomes are isolated and stained with DNA specific dyes and flow sorted based on size and differential dye staining. The flow-sorted chromosomes are then delivered into recipient cells via standard DNA transfection technology, and delivery of intact chromosomes is determined by FISH.

As an alternative, CRISPR editing technologies can be adapted to visualize the synthetic chromosomes and to isolate and purify the synthetic chromosomes prior to delivery to stem cells. (See co-pending patent application PCT/US16/17179.) In this process, unique DNA elements/sequences are incorporated into the synthetic chromosomes during production in the synthetic chromosome production cells. The presence of these unique DNA elements/sequences on the synthetic chromosome permits specific targeting of an engineered, nuclease deficient CRISPR/Cas-fluorescent protein visualization complex (CRISPR/CAS-FP) directly to the synthetic chromosome without binding to native, endogenous chromosomes. Subsequently, the binding of the CRISPR/CAS-FP to the synthetic chromosome provides a means to purify the synthetic chromosome by flow cytometry/flow sorting for eventual delivery into recipient cells. The synthetic chromosome production cells are subjected to mitotic arrest followed by purification of the synthetic chromosome by flow cytometry/flow sorting based on the unique CRISPR-fluorescent tag binding to the synthetic chromosome.

The employment of CRISPR/CAS-FP bypasses the need for using potentially mutagenic chromosome dyes and alleviates the potential contamination of dye-stained endogenous chromosomes contaminating preparations of flow-sorted synthetic chromosomes. In addition, purified synthetic chromosomes bound with CRISPR/Cas-FP can be utilized for assessing the efficiency of delivery of flow-sorted synthetic chromosomes into recipient cells by simple measurement of fluorescent signal quantity in a transfected recipient cell population. Fluorescent proteins of particular use include but are not limited to TagBFP, TagCFP, TagGFP2, TagYFP, TagRFP, FusionRed, mKate2, TurboGFP, TurboYFP, TurboRFP, TurboFP602, TurboFP635, or TurboFP650 (all available from Evrogen, Moscow); AmCyan1, AcvGFP1, ZsGreenl, ZsYellowl, mBanana, mOrange, mOrange2, DsRed-Express2, EsRed-Express, tdTomato, DsRed-Monomer, DsRed2, AsRed2, mStrawberry, mCherry, HcRed1, mRaspberry, E2-Crimson, mPlum, Dendra 2, Timer, and PAmCherry (all available from Clontech, Palo Alto, Calif.); HALO-tags; infrared (far red shifted) tags (available from Promega, Madison, Wis.); and other fluorescent tags known in the art, as well as fluorescent tags subsequently discovered.

Conditions to be Treated

Diseases and conditions where stem cell treatment has been investigated include but are not limited to diabetes, rheumatoid arthritis, Parkinson's disease, Alzheimer's disease, stroke, traumatic brain injury repair, spinal cord injury repair, heart infarction, vision restoration and repair of the cornea, amyotrophic lateral sclerosis, Crohn's disease, and muscular dystrophy.

For example, interest in using hMSCs for tissue engineering has been validated in numerous pre-clinical models and is under evaluation in clinics. Engineered MSCs of the present invention can be applied therapeutically to cartilage defects, osteoporosis, bone fracture, osteonecrosis, large bone defects or non-union fractures, oral and maxillofacial surgeries, treating osteogenesis imperfecta, treating hypophosphatasia, and prevention of cartilage degradation.

For example, osteoarthritis, OA—otherwise called degenerative joint disease—is the most common form of arthritis affecting one-third of the population over 65 years of age. OA is the result of progressive focal loss of the hyaline cartilage of joints with accompanying bony changes. OA is associated with increased mortality in that patients with OA have an increased risk of death due to all causes relative to the general population. In addition, OA is the principal diagnosis in over half of all arthritis-related hospitalizations, with rates of total knee and hip replacements increasing >200% and >100% over the past two decades. The estimated costs for these replacements run in the tens of billions of dollars annually. The vast majority of patients with OA have some movement limitation and OA of the knee is a leading cause of disability among the general population.

Additionally, numerous other age-associated degenerative pathologies also would benefit from stem cell-based regenerative therapies. Cardiovascular disease, including heart failure, is the leading cause of death in the United States with associated costs ranging in the hundreds of billions of dollars annually. Heart failure can lead to acute ischemia with subsequent loss of cardiomyocytes and fibrotic changes. Autologous stem cell transplantation therapies have met with limited success to date due to poor cell survival and retention in the infarcted areas. Stem cells can be induced to transdifferentiate into neural tissue making them suitable for autologous cell replacement therapy for neurodegenerative disorders such as Parkinson's disease and amyotrophic lateral sclerosis. In addition, MSCs, e.g., could be used to treat hematopoietic and gastrointestinal disease following radiation or chemotherapy. In summary, there is strong precedent for use of stem cell replacement therapies in a variety of disorders; thus, rejuvenation of stem cells would improve their efficacy in autologous transplantation therapies for these age-associated pathologies.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Though the Examples below highlight the use of hMSCs, it is to be understood that the exemplified methods may be used to enhance the replication and differentiation capacity of other cell types, including embryonic stem cells, other adult stem cells, and induced pluripotent stem cells as well as provisionally transformed cells and engineered donor cell lines.

Example 1: De Novo Generation of Satellite DNA-Based Artificial Chromosome

For de novo production of synthetic chromosomes, exogenous DNA sequences are introduced into the HT1080 synthetic chromosome production cell line, and, upon integration into the pericentric heterochromatic regions of acrocentric chromosomes, a large-scale amplification of the short arms of the acrocentric chromosome (rDNA/centromere region) is triggered. During the amplification event, the centromere is duplicated resulting in a dicentric chromosome with two active centromeres. Subsequent mitotic events result in cleavage and resolution of the dicentric chromosome, leading to a breakoff of approximately 40-80 Mb in size comprised predominantly of satellite repeat sequences with subdomains of coamplified transfected transgene that may also contain amplified copies of rDNA. The newly generated synthetic chromosome is validated by observation of fluorescent chromosome painting, via the endogenous chromosome tag and synthetic chromosome tag that has been engineered into the HT1080 synthetic chromosome production cell line and/or fluorescent in situ hybridization (FISH).

The day before transfection, the HT1080 synthetic chromosome production cell line cells are split to a density of approximately 1.0 to $1.5 \times 10^6$ adherent cells into 10 cm tissue culture dishes, and the vectors, SPB107 and SPB125, are purified (e.g., using a Qiagen EndoFree Plasmid Maxi Kit), linearized, and the concentration of the vectors is determined for transfection. The cultured HT1080 cells are fed 3-5 hours before transfection. 20-25 µg per 10 cm semiconfluent tissue culture dish is used to transfect the HT1080 cells using, e.g., Invitrogen's Calcium Phosphate Transfection Kit. Cells are maintained for 2-3 days post-transfection at which point they are trypsinized and replated in selective medium, e.g. puromycin at 5 ug/ml. Selective conditions are maintained for 10-14 days with media changed every 2-3 days. Antibiotic resistant clones are picked when a colony reaches 2-3 mm in diameter. Colonies that are well separated are preferred. Cells are removed by use of a cloning cylinder and trypsin, and transferred to a 6-well plate for expansion and characterization.

Example 2: Retrofit BACs Spanning the hTERT, SIRT1 and NFE2L2 Loci

Initially, the RP11-117B23 BAC clone of hTERT, the RP11-22C9 BAC clone of SIRT1, and the RP11-844A8 BAC clone of NFE2L2 (all available through Empire Genomics, Buffalo, N.Y.) as described above will be used.

The BACs are engineered to render them amenable to loading of the artificial chromosome platform as outlined in FIG. 3. Four vectors containing the GFP gene flanked by a pair of unique lox sites for use in retrofitting BACs have been engineered. Each vector contains a unique pair of modified lox site allowing the fluorescent marker gene to be recycled. PCR is used to amplify the lox-GFP-lox (lox-GFP-lox) regions using primers that have homology to the BAC at their 5' ends to generate fragments amenable to loading on the BAC. One primer also contains the attB sequence between the BAC homology sequence and the lox-GFP-lox sequence for subsequent loading of the retrofitted BAC onto hSynC. The PCR products are loaded on the BAC using Red/ET recombination (Gene Bridges, Heidelberg, Germany). BAC clones are assessed for correct integration of the green fluorescent protein gene and attB sites using PCR for predicted junctions.

Example 3: Load BACs onto hSynC Platform Chromosome

Generally, the scheme outlined in FIG. 3 is followed by sequential loading of each BAC onto the hSynC. Once the first BAC is loaded and the chromosome analyzed, cells are transfected with Cre recombinase, resulting in excision of the GFP gene making the clone amenable to loading of the second retrofitted BAC and selection of GFP fluorescent cells by cell sorting. In this way, the GFP cassettes loaded on the BACs are recycled. Following Cre excision, cells are sorted to isolate those that no longer express GFP. Correct excision of the GFP cassette is confirmed by PCR prior to the loading a subsequent BAC. Retrofitted BACs are loaded on the synthetic chromosome using lambda integrase as previously described. Chromosome engineering is done in some experiments in the human HT1080 human cell line. Briefly, the first BAC is transfected, along with the vector encoding lambda integrase, pCXLamIntROK, into HT1080 cells carrying the synthetic chromosome using lipofectamine (ThermoFisher). Following recovery (24-48 hours in culture), the cells are lifted from the cell culture plate and cells exhibiting green fluorescence are sorted into 96-well cell culture dishes. Fluorescent clones are identified and expanded prior to further characterization.

Example 4: Validation of Chromosome Integrity and hTERT, SIRT1, and NFE2L2 Expression Cassettes and Quantification of Copy Numbers of Loci Engineered chromosomes are assessed for correct integration using PCR-based assays that confirm appropriate targeted integration onto the platform chromosome. The presences of resulting attBxattP recombination products (attR and attL junctions) are confirmed by PCR along with subsequent two-color FISH analysis to confirm colocalization of the hTERT and/or SIRT1 construct onto the synthetic chromosome platform. Chromosome engineering is done in a cell line derived from the CHO-based DG44 cell line or the HT1080 cell line as described above. In order to confirm appropriate expression of the introduced hTERT and SIRT1, Taqman assays (Applied Biosystems, Foster City, Calif.) are used to detect hTERT and/or SIRT1 expression; alternatively expression is assayed after transfer of the synthetic chromosome to the hMSCs.

Because the hSync contains multiple attP sites it is possible to get multiple integrations of a single BAC. Quantitative real time PCR assays are used to determine the copy number of the genes of interest loaded onto hSynC. These assays are routinely used to determine copy number of integration events. Taqman assays (Applied Biosystems, Foster City, Calif.) are used to detect expression of the introduced loci. Expression levels are anticipated to roughly correlate with gene copy number. A clone with a single (1) and one clone with multiple (>1) copies of the introduced BAC, $hSynC_{low}$ and $hSynC_{high}$ respectively, are chosen to enter the next round of chromosome engineering. Once all three BACs are loaded on the hSynCs, 8 synthetic chromosomes are created (FIG. 4).

Example 5: Engineer hSynC to Contain the Tetracycline or Cumate Inducible Gene Expression Systems Platform hSynC chromosomes containing either the Tet-On or the Cumate Switch Inducible system (System Biosciences Inc, Mountain View, Calif.) are developed. The Cumate system is based on the bacterial repressor controlling the degradative pathway for p-cymene in *Pseudomonas putida*. High levels of the reaction product, p-cumate, allow binding of the repressor CymR to the operator sequences (CmO) of the p-cym and p-cmt operon. The reverse tetracycline activator protein (rtTA) or CymR is loaded on the hSynC platform chromosomes, and PCR is used to ensure appropriate targeting of the repressors to the hSynC.

Luciferase constructs under the control of either a Tetracycline Responsive Element (TRE) promoter or the CmO are used to assess levels of gene expression following exposure of cells to the inducing agent, either doxycycline or cumate. Briefly, cells are cultured in the presence or absence of the inducing agent prior to being processed for measurement of luminescence (Nano-glo Luciferase Assay System, Promega or BioLux Cypridina Luciferase Assay Kit, New England Biolabs). Clones with no detectable luminescence in the absence of induction and exhibiting the greatest increase in luminescence after induction are chosen for further engineering.

The coding sequences of hTERT, SIRT1, and NFE2L2 as described above are synthesized as a double stranded molecule (Genscript, Piscataway, N.J.). The coding sequences are placed downstream of either a TRE or the CmO regulatory sequence, which is synthesized as part of the same molecule. In-Fusion cloning (Clontech, Mountain View, Calif.) is used to insert these fragments in the pAPP hSynC targeting vector. Therefore, extensions complementary to the vector ends are synthesized at each end of the synthesized DNA molecules. The synthesized DNA molecules are loaded onto vectors, pAPPBAC1 through pAPPBAC4, which have been engineered to contain the attB-lox-GFP-lox cassette making it amenable to loading on the hSynC. (See, e.g., PCT/US2017/027102, entitled "Sequential Loadings of Multiple Delivery Vectors using a Single Selectable Marker" Perkins.) Each lox-GFP-lox cassette contains a unique set of lox sites making the GFP recyclable. Each clone is validated using PCR for recombination junctions and sequencing to ensure the promoters and cDNAs contain no mutations.

Figure 5:
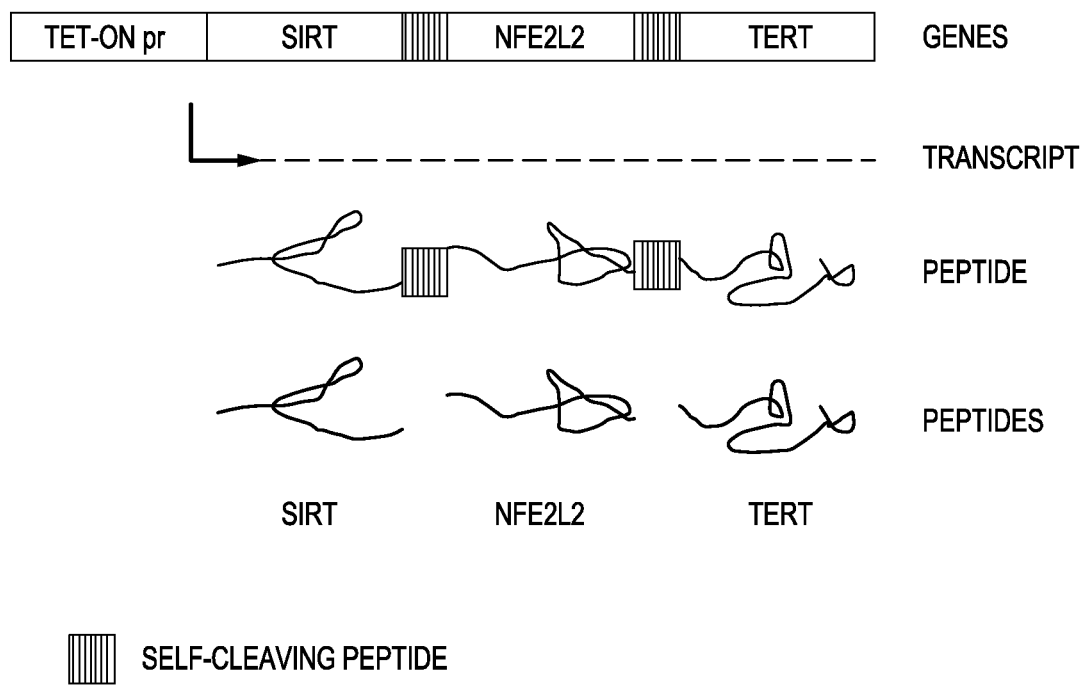
FIG. 5 is a schematic of three genes, SIRT, NFE2L2, and TERT engineered to be transcribed as a single transcript containing self-cleaving peptides between the genes and under the expression control of an inducible TET-ON promoter.

Alternatively, cDNAs of the three genes, SIRT, NFE2L2 and hTERT, may be engineered as a single transcript containing self-cleaving peptides between the genes and under the expression control of an inducible promoter such as Tet-On or the Cumate Switch Inducible system as shown in FIG. 5. In this manner the stoichiometric levels of the three proteins may be maintained and the expression level controlled by inducer. This single vector construction will also include the appropriate repressor for the inducible promoter.

Example 6: Chromosome Transfer

Adipose-derived MSCs are obtained from Lonza and cultured as recommended by the manufacturer. For all experiments using MSCs, the cells are cultured under a physiological oxygen environment (e.g., 3% $O_2$). A low oxygen culture condition more closely recapitulates the in vivo environment and has been demonstrated to extend the lifespan and functionality of MSCs. The validated engineered platform chromosomes are purified away from the endogenous chromosomes of the synthetic chromosome production cells by high-speed, flow cytometry and chromosome sorting and delivered into MSCs by lipid-based transfection reagents. Delivery of intact, engineered ACE platform chromosomes is confirmed by FISH and PCR analysis.

Example 7: Expression of hTERT, SIRT1, and NFE2L2 hTERT expression is confirmed using real time-PCR (RT-PCR). Because hTERT is not expressed in hMSCs, the Taqman assay available from Applied Biosystems (Hs00972649_m1, catalog number 4331182) is used to quantify telomerase expression and directly compare this to hTERT expression in well-characterized human tumor derived cell lines HT1080 and HeLa. Previous work has demonstrated a high concordance between hTERT expression and telomerase activity as measured using the Telomere Repeat Assay Protocol (TRAP) assay. However, to confirm that hTERT expression results in enzymatic activity, protein extracts are prepared from cells using CHAPS detergent buffer and assayed for telomerase activity using the TRAPEZE® RT Telomerase Detection Kit (EMD Millipore) which allows fluorometric detection and real time quantification of telomerase activity.

The level of expression of SIRT1 is assessed by using RT-PCR using assays obtained from Applied Biosystems. In order to differentiate introduced SIRT1 from endogenous SIRT1, silent mutations are engineered into the introduced SIRT1 during gene synthesis and a Taqman assay that can differentiate between introduced and endogenous SIRT1 is employed. A made-to-order TaqMan assay designed to only amplify mRNA produced by the introduced SIRT1 is designed based on the engineered silent mutations, while endogenous SIRT1 is detected using the inventoried TaqMan assay Hs01009006_m1 (catalog number 4331182). Similarly, the level of expression of NFE2L2 is assessed by using RT-PCR. Again, in order to differentiate introduced NFE2L2 from endogenous NFE2L2, silent mutations are engineered into the introduced NFE2L2 during gene synthesis. A made to order TaqMan assay designed to employ the silent mutations is used to detect transcripts derived from the introduced NFE2L2, while transcripts generated from the endogenous NFE2L2 are detected using the inventoried TaqMan assay Hs00975961_g1 (catalog number 4331182).

Example 8: Replicative Lifespan

MSCs have been shown to have a limited lifespan of 20-40 population doublings (PD) depending upon the cell source and culture conditions. Adipose-derived hMSCs have a doubling time of approximately 48 hours. Control and experimental cells are cultured in triplicate. Cells are plated at 5,000 cells/cm$^2$ and medium is changed every third day. When cells reach 50-60% confluency (generally about 2 PD), they are trypsinized and counted prior to replating at 5,000 cells/cm$^2$ for continued culturing. Cells are carefully monitored throughout the experiment for morphological changes indicative of replicative senescence. Total PD achieved as well as time between doublings is assessed to determine the differences between control and experimental MSCs. Replicative senescence is confirmed by assaying for senescence-associated β-galactosidase expression (Cell Signaling Technologies, catalog number 9860) and the presence of senescence-associated heterochromatin foci, a distinct facultative heterochromatin that can be distinguished from both constitutive heterochromatin and other forms of facultative heterochromatin by the presence of specific proteins (e.g., macro histone 2HA, heterochromatin protein 1, and lysine 8 di- or tri-methylated histone H3) and absence of other proteins (e.g., lysine 27 tri-methylated histone H3).

Example 9: Telomere Length

Average population telomere length is quickly assessed by extracting total genomic DNA and applying a quantitative PCR-based telomere length assay using primers described by Cawthorn (*Nucleic Acids Res* 2009; 37:e21). Telomere length of control standardized human cell lines is used to normalize experimental results. DNA concentration for each sample is determined using the Quant-iT PicoGreen dsDNA quantitation assay (Invitrogen). Telomeric DNA is amplified and compared with a standard curve generated from a pooled human genomic DNA control sample (Promega). Relative telomere length is determined from the difference in calculated quantities of each sample compared with the pooled control. Following chromosome transfer, DNA is extracted every other week (i.e., every 4 PD) for 4 months or until cells undergo replicative senescence as is expected for control cells. Differences in telomere length between control and telomerase expressing cells is determined using the t-test. An alternative approach to measuring telomere length at the population level is to use a FISH-based flow cytometric approach (Flow FISH). Telomerase has been shown to preferentially elongate the shortest telomeres in the population. Although this may be sufficient to have a functional effect on replicative lifespan and functionality of MSCs, it may not be possible to detect differences using a population level assessment. Therefore, quantitative FISH is employed, which allows detection of preferential elongation of the shortest telomeres in the population by observing a preferential rightward shift of the telomere length curve. The Telomere PNA FISH kit/Cy3 (Agilent) is used to detect telomere signals. Intensity of telomere signals is measured in individual cells using flow cytometry.

Example 10: Oxidative Stress

Reactive oxygen species (ROS) increase as cells age and oxidative damage is a major contributor to age-associated damage to cells and cellular macromolecules. Telomerase has been implicated as having a telomere independent role in the cellular response to oxidative stress. Every second passage (i.e., every 4 PD), excess cells from the replicative lifespan assay above are combined and used to compare levels of generalized oxidative stress in control and experimental cells using the CellRox Green Flow Cytometry Kit (Thermo Scientific), allowing detection of ROS in living cells using a cell permeable reagent that is non-fluorescent when reduced and highly fluorescent when oxidized. The live cells are distinguished from dead cells using a cell-impermeant red dye. Briefly, cells are resuspended at $1\times10^5$ cells/mL and incubated with the dyes for 60 minutes at 37° C. prior to flow cytometric analysis. As a positive control, an aliquot of cells are incubated with the potent ROS inducer, tert-butyl hydroperoxide (TBHP) and as a negative control cells are incubated with N-acetylcysteine for 1 hour prior to treatment with TBHP.

Example 11: Differentiation

Differentiation potential of MSCs decreases with age and shows a shift from the osteogenic lineage to the adipogenic lineage. Therefore, the differentiation potential of control versus experimental hMSCs is assessed. Differentiation potential prior to chromosome transfer is assessed and set as baseline. The ability of hMSCs to retain osteogenic differentiation relative to adipocytic differentiation is tested using excess cells from the replicative lifespan study every 10 PD. Human MSCs are induced to differentiate using either osteogenic or adipogenic differentiation medium (Lonza) following the recommendations of the manufacturer. After differentiation is complete (approximately 3-4 weeks), cells are assessed for level of differentiation using either the OsteoImage Mineralization Assay or the AdipoRed Adipogenic Assay (Lonza).

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112, ¶6.

We claim:

1. A method for increasing replicative lifespan, differentiation capacity and/or plasticity of mammalian cells comprising:
    transfecting mammalian cells with a stable, non-integrating, self-replicating synthetic chromosome comprising an expression cassette stably integrated into the chromosome, wherein the synthetic chromosome is a human synthetic chromosome, said cassette comprising sequences encoding at least two genes from the group consisting of hTERT, SIRT1 and NFE2L2; and
    expressing the at least two genes from the synthetic chromosome, wherein expression of the genes from the synthetic chromosome in the mammalian cells increases replicative lifespan, differentiation capacity and/or plasticity of the mammalian cells relative to a control.

2. The method of claim 1, wherein the mammalian cells comprise stem cells.

3. The method of claim 2, wherein the stem cells are adult-derived mesenchymal stem cells (MSCs) originating from adipose tissue.

4. The method of claim 2, wherein the stem cells are MSCs originating from bone marrow.

5. The method of claim 2, wherein the stem cells are autologous cells from a subject to be treated.

6. The method of claim 1, wherein the expression cassette comprises an inducible promoter.

7. The method of claim 6, wherein the inducible promoter is selected from a Tet-inducible promoter and a Cumate Switch inducible promoter.

8. The method of claim 1, wherein the expression cassette comprises hTERT clone RP11-117B23.

9. The method of claim 1, wherein the human synthetic chromosome comprises an expression cassette expressing the genomic sequence of SIRT1.

10. The method of claim 9, wherein the expression cassette comprises an endogenous SIRT1 promoter.

11. The method of claim 9, wherein the expression cassette comprises SIRT1 clone RP11-22C9.

12. The method of claim 1, wherein the human synthetic chromosome comprises an expression cassette expressing the genomic sequence of NFE2L2.

13. The method of claim 12, wherein the expression cassette comprises an endogenous NFE2L2 promoter.

14. The method of claim 12, wherein the expression cassette comprises NFE2L2 clone RP11-844A8.

15. The method of claim 1, wherein the human synthetic chromosome is produced via a top down approach.

16. The method of claim 1, wherein the human synthetic chromosome is produced via a bottom up approach.

17. The method of claim 1, wherein the human synthetic chromosome is produced via engineering of naturally occurring minichromosomes.

18. The method of claim 1, wherein the human synthetic chromosome is produced via de novo chromosome generation by targeted amplification of chromosomal segments.

19. The method of claim 1, wherein the mammalian cells are differentiated cells with limited replicative capacity.

20. A method for increasing replicative lifespan, differentiation capacity and/or plasticity of mammalian cells comprising:
    transfecting mammalian cells with a stable, non-integrating, self-replicating synthetic chromosome comprising an expression cassette stably integrated into the chromosome, wherein the synthetic chromosome is a human synthetic chromosome, said cassette comprising sequences encoding all of the hTERT, SIRT1 and NFE2L2 genes; and
    expressing all of the hTERT, SIRT1, and NFE2L2 genes from the synthetic chromosome, wherein expression of the genes from the synthetic chromosome in the mammalian cells increases replicative lifespan, differentiation capacity and/or plasticity of the mammalian cells relative to a control.

21. The method of claim 20, wherein the expression cassette comprises an endogenous hTERT promoter driving expression of hTERT, an endogenous SIRT1 promoter driving expression of SIRT1, and an endogenous NFE2L2 promoter driving expression of NFE2L2.

22. The method of claim 20, wherein the expression cassette comprises an inducible promoter driving expression of all of hTERT, SIRT1, and NFE2L2.

23. The method of claim 22, wherein the inducible promoters are selected from a Tet-inducible promoter and a Cumate Switch inducible promoter.

24. The method of claim 22, wherein the expression cassette comprises cDNAs of the SIRT, NFE2L2 and hTERT genes engineered as a single transcript containing self-cleaving peptides between the genes.

25. The method of claim 20, wherein the hTERT expression cassette comprises hTERT clone RP11-117B23, the SIRT1 expression cassette comprises SIRT1 clone RP11-22C9, and the NFE2L2 expression cassette comprises NFE2L2 clone RP11-844A8.

* * * * *